United States Patent [19]

Young et al.

[11] Patent Number: 5,114,342
[45] Date of Patent: May 19, 1992

[54] SALIVA EJECTOR TIP WITH INTEGRAL VALVE

[76] Inventors: Rily Young, 8681 Luss Dr., Huntington Beach, Calif. 92646; James Shen, 18751 Beach Blvd., Huntington Beach, Calif. 92648

[21] Appl. No.: 607,570

[22] Filed: Nov. 1, 1990

[51] Int. Cl.⁵ .............................. A61C 17/06
[52] U.S. Cl. .................. 433/95; 137/512.4; 604/119
[58] Field of Search ............... 433/91, 95, 96; 251/342, 344, 349; 604/313, 314, 320, 249, 256, 119; 137/512.4, 849

[56] References Cited

U.S. PATENT DOCUMENTS

| | | | |
|---|---|---|---|
| 3,490,488 | 1/1970 | Grist | 137/849 |
| 3,586,068 | 6/1971 | Nicholson | 251/349 |
| 3,841,308 | 10/1974 | Tate | 604/249 |
| 4,534,542 | 8/1985 | Russo | 251/342 |

Primary Examiner—Cary E. O'Connor
Attorney, Agent, or Firm—David Pressman

[57] ABSTRACT

A saliva ejector tip for dental use comprises a tube (10) with a pliable, flexible tip. The end (26) of the tip is flat. The sides of the tip adjacent the end extend down to form a cage (22) of spiral mullions which terminate at a solid base portion of the tip. Extending axially inside the tip from the end is an internal plunger (24). Below the plunger on the inside is an annular valve seat (28). When the end is pushed in, the cage collapses and the plunger is pushed into the valve seat which it closes off so as to close the tip. In this manner the tip can be closed with one hand when it is removed from the mouth, thereby to avoid a sucking sound, and the need for the dentist to handle and contaminate the more proximal hose and hose valve, which are difficult to sterilize. The mullions of the cage can be extended down over the base of the tip (FIG. 4) to provide lands (32) on the base for an easier grip and saliva routing action.

16 Claims, 1 Drawing Sheet

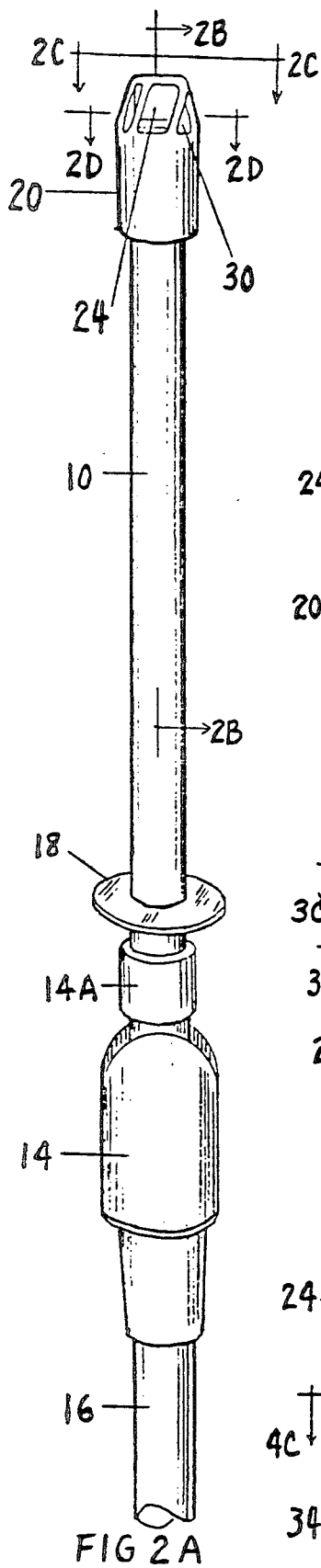
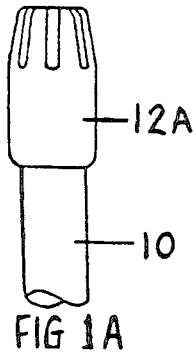
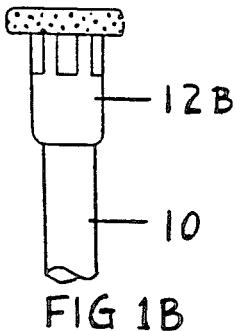
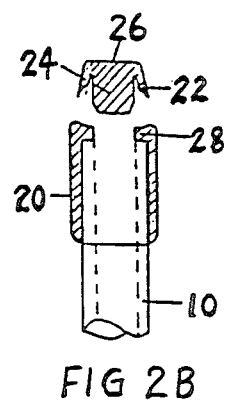
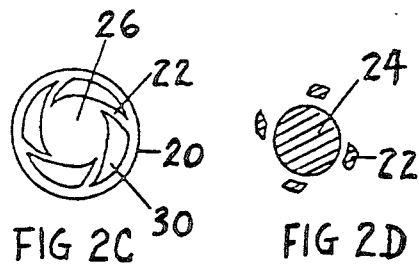
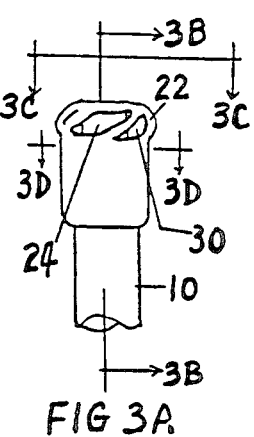
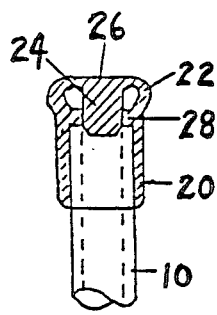
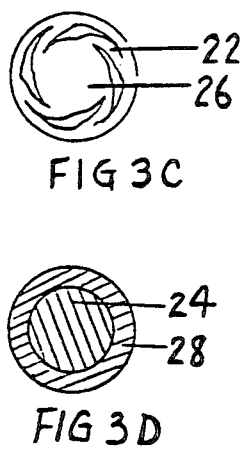
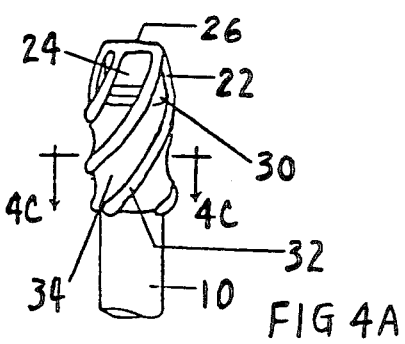
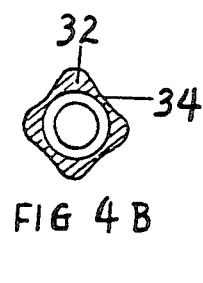

SALIVA EJECTOR TIP WITH INTEGRAL VALVE

CROSS-REFERENCE TO RELATED APPLICATION

This invention is related and complimentary to the invention of our copending application, Ser. No. 07/592,360, Filed Oct. 3, 1990.

FIELD OF INVENTION

This invention is in the field of dental instruments, specifically the area of dental saliva ejectors and the reduction of microorganism transmission.

PRIOR ART

As indicated in our above-referenced copending application, despite the precautions and measures taken by dentists to keep their instruments sterile, many of their practices and instruments allow undesired MicroOrganisms (MOs), including viruses, bacteria and fungi, to enter their patients' mouths. These MOs generally come from other patients and are known as cross-contaminants since they travel across from one patient to another. They usually make the inter-patient trip via the air, the dentist's hands, dental instruments, instrument hoses, and instrument holders, as will be shortly discussed. Such cross-contamination was most undesirable in the past because it spread infectious diseases, such as influenza, colds, hepatitis, etc. However it is extremely undesirable now because of its ability to spread the lethal AIDS virus.

In order to understand the modality of cross-contamination, refer to FOGS. 1A and 1B, side views of typical prior-art saliva and debris suction removal instruments, also known as saliva ejectors (SEs). Such SEs comprise a tube 10 whose proximal (lower) end is connected via a hose valve and hose (similar to valve 14 and hose 16 of FIG. 2A) and then to a vacuum source (not shown). The distal (upper) end of each tube is fitted with a strainer tip, i.e., the tube of FIG. 1A is fitted with tip 12A (rounded end) and tube 10 of FIG. 1B is fitted with tip 12B (padded end). During a dental procedure, an SE, such as the ones of FIGS. 1A and 1B, is inserted into the patient's mouth to remove by suction saliva and small particles, such as excess filling material, ground-away old fillings and decay, etc.

Tube 10 is made of flexible plastic and usually has a molded-in-place internal wire core (not shown). This wire enables the tube to hold any shape to which it is bent (usually U-shaped) so that it will stay in position in the patient's mouth while the dentist or hygienist (hereinafter "DP" for Dental Professional) performs various procedures, such as cleaning and filling, in such mouth.

During dental procedures, MOs from the patient's mouth are deposited directly on tube 10, tips 12, and the fingers (not shown) of the DP because these are inserted directly into the mouth. Also the DP's fingers and the DP's other instruments accumulate MOs from the airborne water mists due to splattering caused when an air-water syringe is used to rinse operative sites and other areas worked on. The DP's fingers also accumulate MOs because they handle tube 10 and tips 12 and other dental instruments, such as scalers, curettes, pliers, etc., which are also introduced into the mouth where they are directly contaminated by MOs.

When the SE is in the patient's mouth, as stated, a vacuum is applied thereto via a hose and valve (similar to those shown in FIG. 2A) in order that tips 12 will be able to collect the saliva and debris. However when the SE is removed, e.g., for the patient and/or DP to rinse, rest, go to the bathroom, etc., it is desirable to stop the vacuum since the tip will make a disturbing and loud unnecessary hissing noise when it is out of the mouth. Also it will suck air from the general room area, causing airborne contaminants to be deposited on the moist tip, where they will remain and possibly infect and contaminate the patient. Thus it is desirable occasionally to stop the vacuum applied to the tips.

To turn off the vacuum, the DP must handle the hose valve. However by doing this, the DP's MO-laden or contaminated fingers will deposit MOs onto this valve and the hose to which it is connected, thereby contaminating these parts.

When the patient's treatment is completed, the DP will remove and discard tube 10 and its tip 12A or 12B, but will leave the hose and hose valve in place. The hose is too expensive to be replaced for each patient. Since the hose valve is permanently attached to the hose, it to cannot be replaced easily. Also valves are time consuming and difficult to detach and attach to their hoses and thus it is undesirable to change them for each patient. Furthermore the hose is too sensitive to heat to be autoclaved and, while it could be chemically sterilized, such a procedure takes about eight hours and requires space, chemicals, valuable time, etc.

When a new SE is attached for the next patient, the DP will change gloves, wash his or her hands, and insert the SE in the patient's mouth as before. Thereafter the DP will have to turn off the hose valve periodically, as before. In doing this, the DP will recontaminate his or her fingers by touching the hose and hose valve which were contaminated from the previous patient. Thus when the DP's fingers are inserted into the new patient's mouth, MOs from the previous patient will cross-contaminate the new patient, via the equipment and the DP's fingers. As stated, this cross contamination is very undesirable because it spreads diseases.

OBJECTS AND ADVANTAGES

Accordingly, several objects and advantages of the invention are to provide a way to prevent MOs of one patient's mouth from entering other patients' mouths, to reduce the spread of infectious diseases, including the AIDS virus, in dental environments, to prevent cross-contamination of dental patients by MOs, to prevent MOs from cross-contaminating patients via dental instruments, their holders, and/or the fingers of dental personnel, to prevent such cross-contamination with dental ejectors, to prevent the rushing sound which occurs when a SE is removed from a patient's mouth, and to avoid the need to turn off the vacuum source or the hose valve during this operation.

Other objects are to avoid the need to chemically or thermally sterilize dental fluid hoses and valves, to provide a viable alternative to all non-sterilizable instrument holders, and to provide a tip valve which is atraumatic to mucosa, which is patient friendly, less intimidating, and more comforting to patients.

Further objects and advantages will become apparent from a consideration of the ensuing description and the accompanying drawings.

DRAWING FIGURES

FIGS. 1A and 1B are side views of prior-art saliva ejection tips and attached tubes. .

FIG. 2A is a side view of an open saliva ejection valve according to the invention, together with an attached tube, hose valve, flange guard, and hose. FIG. 2B is a side sectional view of the tip valve of FIG. 2A taken in the direction indicated by lines 2B—2B in FIG. 2A. FIG. 2C is a top view of the tip valve of FIG. 2A taken in the direction indicated by lines 2C—2C in FIG. 2A. FIG. 2D is an axial sectional view of the tip valve of FIG. 2A taken in the direction indicated by lines 2D—2D in FIG. 2A.

FIG. 3A is a side view of the valve of FIG. 2A in closed condition. FIG. 3B is a side sectional view of the valve of FIG. 3A. FIG. 3C is a top view of the valve of FIG. 3A taken in the direction indicated by lines 3C—3C in FIG. 3A. FIG. 3D is an axial sectional view of the valve of FIG. 3A taken in the direction indicated by lines 3D—3D in FIG. 3A.

FIG. 4A is a side view of a valve similar to that of FIG. 2A, but with a modified external structure. FIG. 4B is an axial sectional view taken in tie direction indicated by lines 4C—4C of FIG. 4A.

DRAWING REFERENCE NUMERALS AND ABBREVIATIONS

| | |
|---|---|
| 10 tube | 12 (A & B) tip |
| 14 hose valve | 16 hose |
| 18 flange guard | 20 tip valve |
| 22 cage | 24 plunger |
| 26 end | 28 valve seat |
| 30 opening | 32 lands |
| 34 grooves | |
| SE saliva ejector | DP dental professional |
| HDPE high density polyethylene | MO microorganism |

DESCRIPTION-OPERATION—FIGS. 2A-2D—SALIVA EJECTOR WITH OPEN VALVE

In accordance with the invention, we provide a saliva ejector (SE) with a built-in tip valve so that it can be turned off locally by the DP or the patient, thereby avoiding the need to handle the hose valve and hose. The tip valve comprises a strainer tip which is flexible enough to be collapsed. It has an integral plungerlike internal axial obturator and internal annular valve seat which mate to close the valve when the tip is collapsed.

A side view of an SE assembly in an open state is shown in FIG. 2A. The SE comprises the usual tube 10 (preferably made of HDPE—high density polyethylene) attached to a hosel 14A of hose valve 14, which is in turn attached to hose 16. The proximal (lower) end of tube 10 preferably has a guard flange 18 in accordance with the invention of our above copending application to prevent the DP from inadvertently touching and contaminating the non-disposable parts (valve 14 and hose 16). At the distal end of tube is an SE tip or tip valve 20 which is cemented or force fit onto tube 10. Tip 20 is made of a flexible, soft plastic, e.g., of SANTOPRENE ™ thermal plastic elastomer (Monsanto Chemical Co., Akron, OH) or neoprene. It should be similar in softness and flexibility to the material used for the suction bulb of medicine droppers or the nipple or teat of baby bottles or pacifiers. It is about 15 mm long, with all components sized proportionately.

The base or proximal (bottom) half of tip 20 is solid and its distal (upper) half is formed into a cage or strainer 22. Cage 22 comprises a plurality of elongated mullions or web portions with a slight helical twist. An internal plungerlike axial obturator 24 inside the cage has a distal end integrally attached to the inside of the tip's flat end 26. End 26 is supported by the mullions of cage 22.

As shown in the sectional view of FIG. 2B, plunger 24 comprises an elongated, solid, cylindrical member with a tapered bottom or proximal end. An annular internal valve seat 28 is attached integrally to the inside of the solid bottom half of tip 20 so as to form an internally projecting circular ledge. As shown in FIG. 2B, the lower surface of seat 28 abuts the top end of tube 10 and thus forms a stop to limit insertion of tube 10 into tip 20. Also the top of tube 10 supports seat 28.

Note from the end view of FIG. 2C that end 26 of tip 20 is circular and solid and that the mullions of cage 22 curve down from end 26 to the base of the tip in a clockwise direction. Each pair of adjacent mullions is separated by an open space 30; these open spaces form a plurality of intake holes. Plunger 24 is circular in shape (FIG. 2D) and the mullions of cage 22 surround plunger 24.

The tip is shown in its open or transmissive state in FIGS. 2A to 2D. When a vacuum is applied to hose 16, and assuming hose valve 14 is also open, the vacuum will suck air in continuously through openings 30 of cage 22. The inrushing air will pass around plunger 24, through seat 28, and through the lumen of tube 10. Thus when the tip is in its open state, it can be used in the same manner as the prior-art tips of FIGS. 1A and 1B to remove saliva and debris from a patient's mouth. Tube 10 can be bent as desired, usually in a U shape, so that the SE can be hung over the patient's lower front teeth to keep the tip at the floor of the mouth.

DESCRIPTION—FIGS. 3A-3D—SALIVA EJECTOR WITH TIP VALVE CLOSED

To close the tip valve, the DP or the patient merely pushes down (FIGS. 2A or 2B) on end 26 of the SE. This will cause the tip's cage 22 to collapse as shown in FIG. 3A. The mullions will thus bulge out slightly. Plunger 24 will move in an axial downward direction to the closed or obturating position of FIG. 3B where it mates with seat 28 and thereby closes off the opening formed by seat 28, as shown in the sectional view of FIG. 3D. The tip will hold this position since plunger 24 will make a force fit with seat 28: its diameter (4.75 mm) is slightly greater than the internal diameter of seat 28 (4.5 mm). Also the vacuum will help hold the tip closed. When the tip is so pushed down or closed, openings 30 will also partly close (FIG. 3A and end view of FIG. 3C) and the tip will become shorter; its length will be reduced to about 11 mm.

The DP (or patient) can collapse the tip with an easy, simple, and quick push of an index finger when the SE is removed from the patient's mouth. The DP can do this with one hand by grasping the base of the valve of tube 10 with the thumb and fingers and using the index finger to push in the top, in a manner similar to pushing the button at the top of a ballpoint pen. To re-open the tip valve, the DP merely holds tube 10 or the base of the valve with one hand and pulls up on the cage or distal portion of the tip with the other hand (or the thumb and index finger of the same hand) to restore it to the condition of FIG. 2A. The tip valve, when opened, will remain open since the mullions of the cage are molded in and thus have a tendency to remain in their open state. Alternatively the patient can close the valve by pushing end 26 against his or her front teeth. The patient can also open the valve by holding it in one hand and pulling the cage open with his or her front teeth.

DESCRIPTION—FIGS. 4A–4B—SALIVA EJECTOR WITH LANDS ON BASE

Instead of terminating at the base portion of tip valve 20, the mullions of cage 22 can be continued down over the outside of the base portion to form spiral lands or flutes 32 over such base portion, as shown in FIGS. 4A and 4B. The portions of the base between lands 32 are recessed so as to form grooves 34. These lands make the tip more attractive. They also provide functional benefits: they appear to help direct saliva flow from the proximal portion of the tip to holes 30 at the distal end of the tip, help retract mucosa away from the tip to prevent it from blocking the holes in the cage, and provide an easier-to-grasp surface on the base.

SUMMARY, RAMIFICATIONS, AND SCOPE

The reader will thus see that we have provided a saliva ejector with a built-in valve so that the SE itself can be closed. Thus the DP does not have to touch the non-sterilizable or difficult-to-sterilize hose valve or shut off the vacuum when the SE is removed from a patient's mouth. This will aid in preventing MOs from travelling between patients' mouths, thereby reducing the spread of infectious diseases, including AIDS. The SE can be made economically, it is reliable and easy to use, it is simple and safe in operation, and it is very comfortable due to its softness.

While the foregoing specification and accompanying drawing contain many specificities, these should not be considered as limitations on the invention since many variations are possible within its scope. For example the SE can be made of other materials than as indicated, the shape of the plunger and seat can be made non-circular, such as square, triangular, polygonal, etc. The shape of the mullions of the cage can be changed from helical to straight axial. Also the cage can have round, square, or holes of other shapes. The grooves in the embodiment of FIG. 4 can be convex rather than concave. The end of the SE can be convex or concave, rather than flat. The valve need not be at the end of a tube, but can be in an intermediate position along the length of the tube so that the intake holes are in the side of the tube and the valve (and tube) can be closed by squeezing the tube together from both sides of the holes to shorten the tube. The tip valve is not limited to dental use, but can be used for other applications, such as siphon tube end valves, general suction pump hose valves, etc. The tip valve can be used to close of an outflow of fluid, rather than an inflow, in which case the tube would be connected to a source of fluid pressure which is higher, rather than lower, than the ambient pressure outside the valve. The tip valve can be sold separately from the tube so that the user can install it on any tube, preferably by cementation, but also by friction or snap fit. Also the tip valve can be integral with the tube.

Accordingly the full scope of the invention should be determined by the appended claims and their legal equivalents, and not by the examples given.

We claim:

1. A suction tip and valve, comprising:
   an elongated tubular housing having an axial lumen therein, one end of said tubular housing being closed by an end surface which is perpendicular to said lumen, the other end of said lumen comprising means for attachment to a source of fluid at a different pressure than ambient pressure outside said housing,
   said housing having a side having a portion containing a plurality of openings, said openings being separated by web portions,
   said housing containing an internal annular valve seat on one side of said portion thereof,
   an inside surface of said end surface having one end of an elongated obturator attached thereto, the other end of said obturator being shaped to mate with and close said valve seat, said obturator being shaped so that it is normally spaced from said valve seat so that fluid can pass through said plurality of openings to said other end of said lumen, said web portions being flexible so that they can be collapsed so as to allow said obturator to move toward and mate with and close said valve seat so that fluid cannot pass through said plurality of openings to said other end of said lumen.

2. The suction tip and valve of claim 1 wherein said web portions comprise elongated mullions.

3. The valve of claim 2 wherein said mullions extend over said side wall of said tubular housing on another side of said portion of said side wall so as to form a plurality of external lands on said side wall.

4. The suction tip and valve of claim 1 wherein said mullions are helically shaped.

5. The suction tip and valve of claim 1, further including a tube attached to said other end of said lumen.

6. A valve for use within a tube to close off an opening in said tube, comprising:
   a tubular housing having an encircling side wall and a lumen within said housing,
   a portion of said side wall having at least one hole therein,
   said tubular housing containing an internal valve seat on one side of said portion of said side wall,
   said tubular housing also containing an obturator mounted on the other side of said portion of said side wall,
   said obturator being shaped and positioned so that if said obturator is moved into said valve seat, it will conformingly mate with said valve seat and close said seat and obturate said lumen,
   said portion of said side wall of said tubular housing being flexible and pliable so that it can be collapsed axially so as to cause said obturator to mate with said valve seat,
   said portion of said side wall of said tubular housing also comprising a plurality of mullions which are oriented in parallel with said lumen, the space between adjacent mullions being open so as to provide a plurality of holes similar to said one hole in said side wall.

7. The valve of claim 6 wherein said tubular housing terminates on said other side of said portion of said side wall.

8. The valve of claim 6 wherein said mullions extend over said side wall of said tubular housing on said one side of said portion of said side wall so as to form a plurality of external lands on said side wall.

9. The valve of claim 6 wherein said obturator comprises an elongated member oriented in parallel to said lumen, one end of said elongated member being free and positioned in said lumen, the other end of said elongated member being attached to said tubular housing.

10. The valve of claim 9 wherein said tubular housing terminates in an end face on said other side of said portion of said side wall, said other end of said elongated member being attached to an inside side of said end face.

11. The valve of claim 6 wherein said tubular housing terminates in an end face on said other side of said portion of said side wall and said obturator comprises an elongated member which is oriented in parallel to said lumen, said elongated member having first and second ends, said first end being free and positioned in said lumen, said second end being attached to an inside side of said end face.

12. The valve of claim 6 wherein said mullions are helically shaped.

13. The valve of claim 12 wherein said tubular housing terminates in an end face on said other side of said portion of said side wall, said obturator comprising an elongated member, one end of which is free and positioned in said lumen, the other end of said elongated member being attached to an inside side of said end face.

14. In a dental saliva ejector of the type comprising:
a tube having an end portion and a side, said tube having a plurality of holes in said side thereof, said holes being separated by respective web portions,
said web portions being sufficiently flexible that said end portion can be shortened by pushing said tube in from an end thereof so as to cause said web portions to shorten, and
means within said tube for obturating said tube in response to said end portion being so shortened,
said means comprising an annular valve seat within the lumen of said tube and an elongated obturator within said tube attached to an inside of said end of said tube,
said elongated obturator being shaped to conformingly mate with said valve seat.

15. The ejector of claim 14 wherein said web portions comprise elongated mullions which are oriented in a direction generally parallel to the direction of elongation of said tube.

16. The ejector of claim 14 wherein said end portion of said tube is a separate valve tip member which is attached to said tube and is of a material which is softer than said tube.

* * * * *